(12) United States Patent
Watkins et al.

(10) Patent No.: US 11,857,498 B2
(45) Date of Patent: *Jan. 2, 2024

(54) SYRINGE SYSTEM

(71) Applicant: Indivior UK Limited, Hull (GB)

(72) Inventors: Andrew Watkins, Richmond, VA (US); Qi Li, Richmond, VA (US); Richard L. Norton, Richmond, VA (US); Daniel Barnhill, Richmond, VA (US); Trant Holt, Richmond, VA (US)

(73) Assignee: Indivior UK Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,887

(22) Filed: Sep. 19, 2022

(65) Prior Publication Data

US 2023/0149262 A1    May 18, 2023

Related U.S. Application Data (63) Continuation of application No. 16/041,170, filed on Jul. 20, 2018, now Pat. No. 11,478,407.

(60) Provisional application No. 62/685,786, filed on Jun. 15, 2018.

(51) Int. Cl.
  *A61J 1/20*    (2006.01)
  *A61M 5/178*   (2006.01)
  *A61M 5/31*    (2006.01)

(52) U.S. Cl.
  CPC .......... *A61J 1/2089* (2013.01); *A61M 5/1782* (2013.01); *A61M 5/3135* (2013.01); *A61M 2205/02* (2013.01)

(58) Field of Classification Search
  CPC ... A61J 1/2089; A61M 5/1782; A61M 5/3135
  See application file for complete search history.

(56) References Cited

U.S. PATENT DOCUMENTS

| | | | |
|---|---|---|---|
| 11,478,407 | B2 | 10/2022 | Watkins et al. |
| 2002/0143271 | A1 | 10/2002 | Crawford et al. |
| 2006/0079834 | A1 | 4/2006 | Tennican et al. |
| 2009/0169872 | A1 | 7/2009 | Krongauz et al. |
| 2011/0060361 | A1 | 3/2011 | Schweiss et al. |
| 2013/0165853 | A1* | 6/2013 | Kawamura ........... A61M 5/346 604/82 |
| 2017/0290987 | A1* | 10/2017 | Mandaroux ....... A61M 5/31505 |
| 2017/0319438 | A1* | 11/2017 | Davis ................. A61M 39/1011 |

FOREIGN PATENT DOCUMENTS

JP    2018/023613 A    2/2018

OTHER PUBLICATIONS

International Search Report dated Nov. 4, 2019, for PCT Application No. PCT/US2019/037317, filed Jun. 14, 2019, 3 pages.
Written Opinion dated Nov. 4, 2019, for PCT Application No. PCT/US2019/037317, filed Jun. 14, 2019, 7 pages.

* cited by examiner

*Primary Examiner* — Dung T Ulsh
(74) *Attorney, Agent, or Firm* — Mintz Levin Cohn Ferris Glovsky and Popeo, P.C.

(57) ABSTRACT

A medication component mixing system is formed of a first syringe, such as a female syringe, and a second syringe such as a male syringe, wherein the system is configured to mix a female portion and a male portion of the medication. The female syringe and the male syringe mechanically couple to one another in an end-to-end fashion for mixing of the contents of the female and male portions.

23 Claims, 13 Drawing Sheets

SYRINGE SYSTEM

CROSS REFERENCE TO RELATED APPLICATIONS

This application is a continuation of U.S. patent application Ser. No. 16/041,170 filed Jul. 20, 2018, which claims the benefit of U.S. Provisional Application Ser. No. 62/685,786, filed on Jun. 15, 2018, the entire contents of which are incorporated herein by reference in their entirety.

BACKGROUND

Certain medications have separate components that are mixed prior to administration to a patient. In such situations, a syringe kit can be used wherein the kit includes two syringes that couple to one another. A first syringe contains the first component of the medication and the second syringe contains the second component of the medication. In an example, the first component is in a dry powder form and the second component is in a liquid form. Such two-component syringe systems are necessary when medication components are not compatible with both (i) each other, as well as (ii) syringe component materials, under extended or accelerated storage conditions.

In order to mix the two components, the first syringe is mechanically coupled to the second syringe so that the syringes are interlocked with one another. The contents of the two syringes are pushed back and forth, in an alternating manner, between the two syringes such as by actuating plungers associated with the first and second syringes. In this manner, the first and second components are mixed together. After such mixing, the syringes are decoupled from one another and an injection needle can then be attached to whichever syringe contains the resultant mixture. The mixed medication can then be administered to a patient, such as via a subcutaneous injection into the patient.

The low cost and pliability of polypropylene make it very common as a material used in the manufacturing of syringes. However, certain solvents (E.g., N-methyl pyrrolidone) leach through polypropylene under long term storage conditions. While cyclic olefin copolymers (COC)/cyclic olefin polymers (COP) do not leach solvents under long term storage conditions, when irradiated, COC/COP can become more brittle. Brittleness can lead to syringe failure during the syringe assembly. COC/COP is also more expensive than polypropylene, making its use not as cost effective.

Current drug mixing systems that use such first and second syringes can sometimes achieve improper mixing of the first and second drug components, as described more fully below. In view of this, there is a need for improved systems for mixing components of a medication.

SUMMARY

A two-component syringe system includes two components configured to couple with each other to mix the contents of each syringe. The coupling occurs in a male-female relationship in an end-to-end fashion.

The female syringe is structurally equipped with a lug-type thread configuration that ensures the female syringe and the male syringe can be coupled to one another in a manner that, after assembly, does not impede proper mixing of the contents. In addition, the female syringe has an extended-length female member, or neck, relative to a corresponding length of a prior art female syringe. The extended-length female member ensures that a complementary male member of the male syringe does not extend too far into the female syringe after coupling and impede full and proper advancement of a plunger of the female syringe. This greatly increases the likelihood that the contents of the female and male syringe of the medication are properly mixed by eliminating dead spaces after coupling in the female syringe.

In a specific aspect, the male member is tapered with a smaller diameter at the tip relative to the base, while the lumen of the female member matches the taper of the male member. In another specific aspect, the female system further provides for a lug thread in the neck of the female syringe, such that when coupled with a COC/COP male syringe, the tapered male and female coupling interface with cause the lug threads to "slip" after tightening to avoid excess tightening. The slipping releases any excess torque from overtightening, which could otherwise be absorbed by the more brittle COC/COP male syringe, possibly resulting in breakage and syringe failure. In alternative embodiments, the COC/COP syringe can be replaced with a syringe formed from polycarbonate or glass syringe; while the polypropylene syringe can be replaced with one fashioned from polyethylene, such as high-density polyethylene (HDPE) or low density polyethylene (LDPE). Other materials can be used for manufacturing of the components.

In another aspect, there is disclosed a female syringe system, comprising: a female syringe formed of: a barrel member defining an internal cavity and having an internal, proximal-most edge that defines a proximal-most edge of the cavity, the barrel member having a proximal opening through which contents can be expelled from the internal cavity; a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and a tapered female coupler on a proximal region of the barrel member, the female coupler having an opening that receives a complementary tapered male member of a male syringe to couple the female syringe with the male syringe, wherein the female member has a structural configuration that prevents the male member of the male syringe from protruding into the internal cavity of the barrel member when the male syringe is coupled to the female syringe.

In another aspect, there is disclosed a female syringe system, comprising: a female syringe formed of: a barrel member defining an internal cavity and having an internal, proximal-most edge that defines a proximal-most edge of the cavity, the barrel member having a proximal opening through which contents can be expelled from the internal cavity; a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and a female coupler on a proximal region of the barrel member, wherein the female coupler couples to a male member of a male syringe, wherein the male syringe includes a concentric sleeve that surrounds the male member, and wherein the male member is longer in length than the sleeve such that a tip of the male member extends past a tip of the sleeve, and wherein the male coupler and female coupler have complementary tapers that limit a depth of insertion of the male member into the female member.

Other features and advantages should be apparent from the following description of various implementations, which illustrate, by way of example, the principles of the disclosure.

DETAILED DESCRIPTION

A medication component mixing system formed of a first syringe, such as a female syringe, and a second syringe, such as a male syringe, wherein the system is configured to mix a female portion and a male portion of the medication. The female syringe and the male syringe mechanically couple to one another in an end-to-end fashion for mixing of the contents of the female and male portions. The female syringe includes a female coupler that mechanically couples to a corresponding male coupler of the male syringe. The female coupler includes a lug-type thread configuration that ensures the female syringe and the male syringe can be coupled to one another in a manner that does not impede proper mixing of the components. The female coupler is configured to prevent the male coupler of the male syringe from impeding proper advancement of a plunger of the female syringe during mixing.

Figure 1:
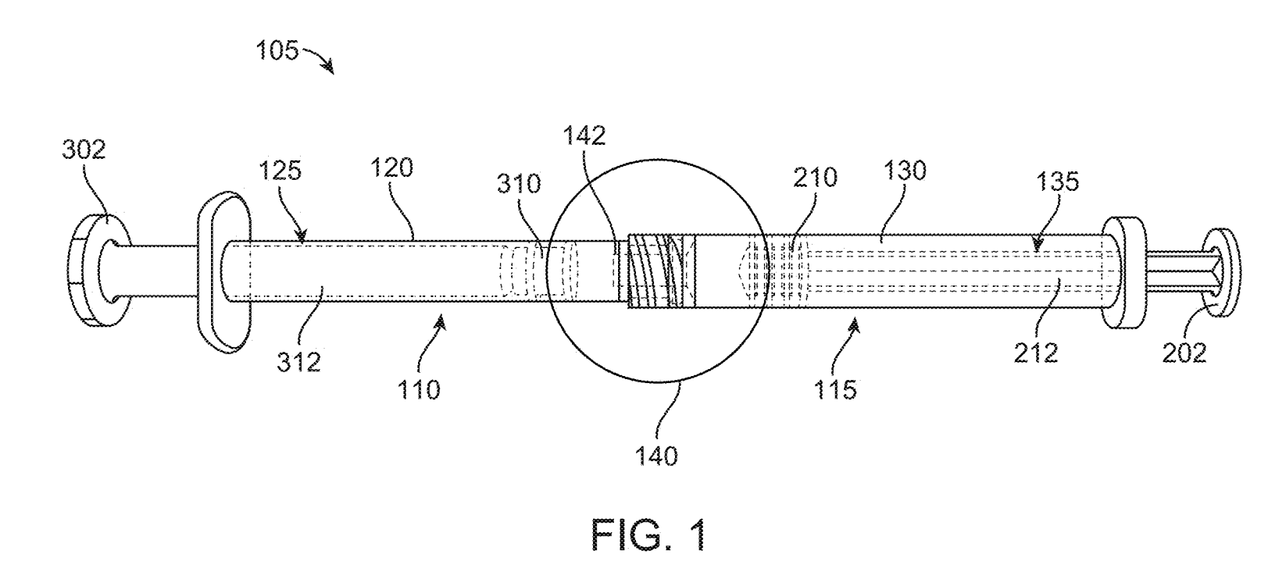
FIG. 1 shows a prior medication component mixing system.

FIG. 1 shows a side view of a prior art medication component mixing system 105 that includes a first syringe and a second syringe. In a non-limiting example, the first syringe is a female syringe 110 configured to contain at least one component of the medication. The second syringe is a male syringe 115 configured to contain at least a second portion of the medication. The female syringe 110 and the male syringe 115 mechanically couple to one another in an end-to-end fashion for mixing of the separate components of the medication between the female syringe 110 and the male syringe 115, as described below. As described in more detail below, each of the female syringe 110 and the male syringe 115 includes a corresponding plunger assembly that can be used to expel contents from the respective syringe. The plunger assemblies are described in detail in FIGS. 2 and 3. The syringes mechanically couple at a coupling location identified within a circle 140 in FIG. 1. The terms "distal" and "proximal" are used herein in relation to the coupling location.

The female syringe 110 is formed of an elongated barrel 120 that defines an internal cavity that holds contents (E.g., powder). A plunger rod assembly 125 of the female syringe 110 includes a plunger rod 312 with a plunger rod cap 302 and a proximal plunger 310. At least a portion of the plunger rod assembly 125 is slidably positioned inside the barrel 120 and can be actuated to push the contents out of the barrel though an opening in the end of the barrel 120.

With reference still to FIG. 1, the male syringe 115 is formed of a barrel 130 that defines an internal cavity that holds contents (E.g., liquid). A plunger rod assembly 135 includes a plunger rod 212 with a plunger rod cap 202 and a proximal plunger 210. At least a portion of the plunger rod assembly 135 is slidably positioned inside the barrel 130 and can be moved within the barrel to push contents (e.g., liquid) out of the barrel 130 though an opening in the end. The barrels 130 and 120 are each formed of elongated bodies. In non-limiting examples, the elongated bodies are cylindrical although the shape may vary.

When coupled as shown in FIG. 1, the respective openings at the end of the barrels 130 and 120 interlock with one another, providing a junction, so that contents can be transferred between the barrels. In addition, the barrels 130 and 120 are co-axially aligned along a common longitudinal axis when coupled to one another. The plunger rod assemblies 125 and 135 can then be actuated in an alternating manner to move the contents of the barrel 120 and the barrel 130 back and forth into one another via the coupling junction to achieve mixing of the contents. However, the male coupler 205 (shown as hidden lines) of the male syringe 115 extends into the cavity of the barrel 120 at a location 142 in the female syringe 110 as shown in circle 140.

Figure 2:
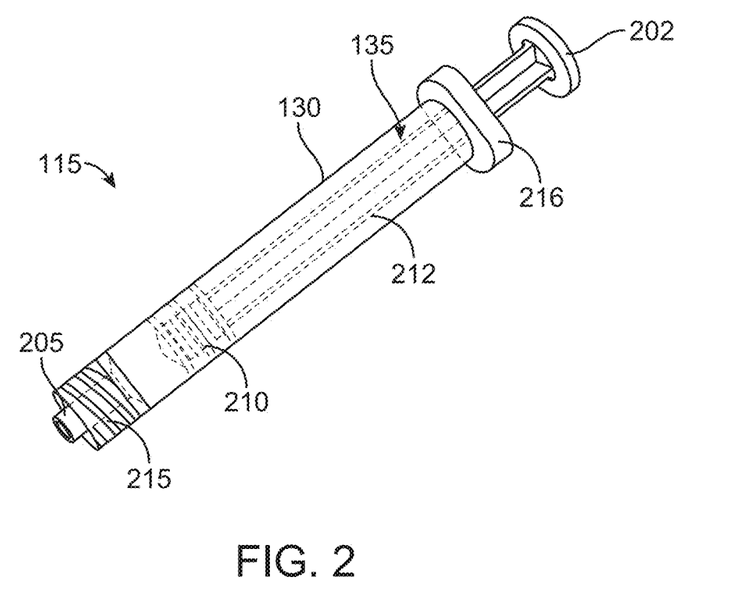
FIG. 2 shows a male syringe of the medication component mixing system of FIG. 1.
Figure 3A:
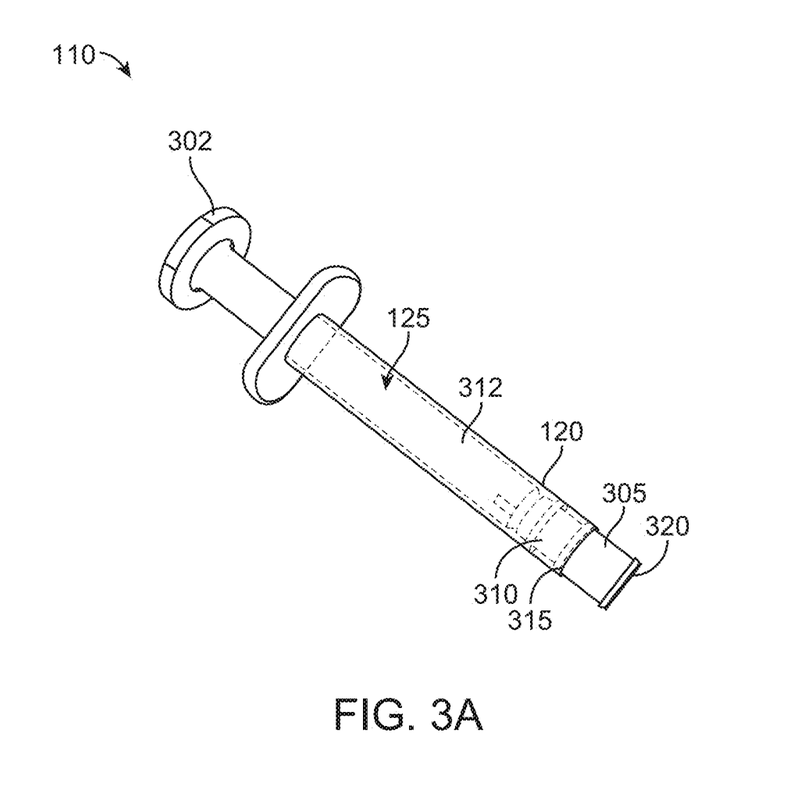
FIG. 3A shows a prior art female syringe of the medication component mixing system of FIG. 1.
Figure 10:
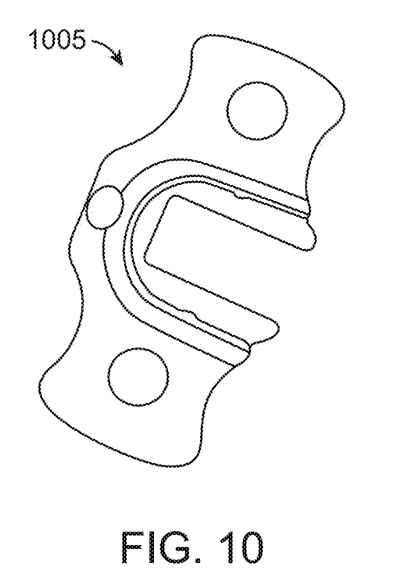
FIG. 10 shows a flange extender.
Figure 11:
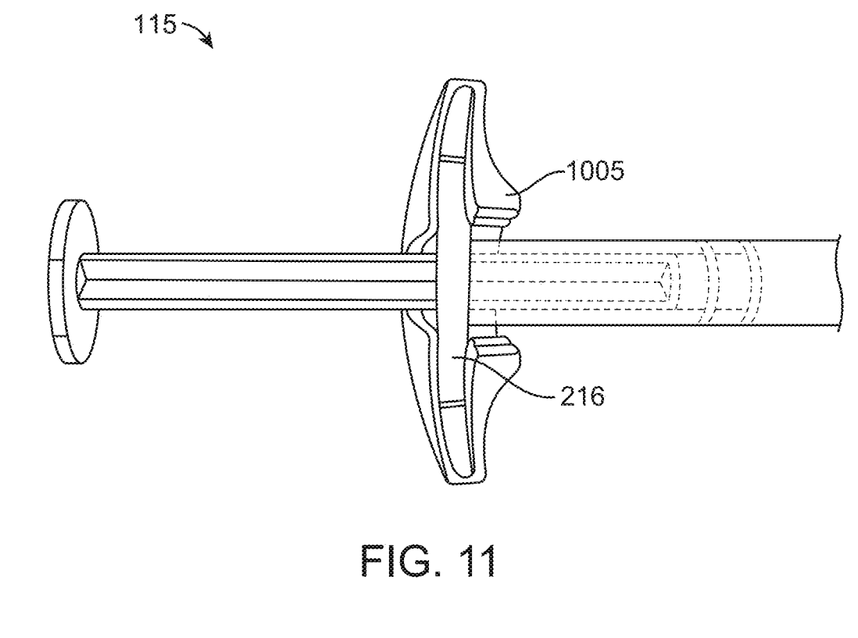
FIGS. 11 and 12 shows the male syringe with the flange extender coupled to a distal flange of the male syringe.
Figure 12:
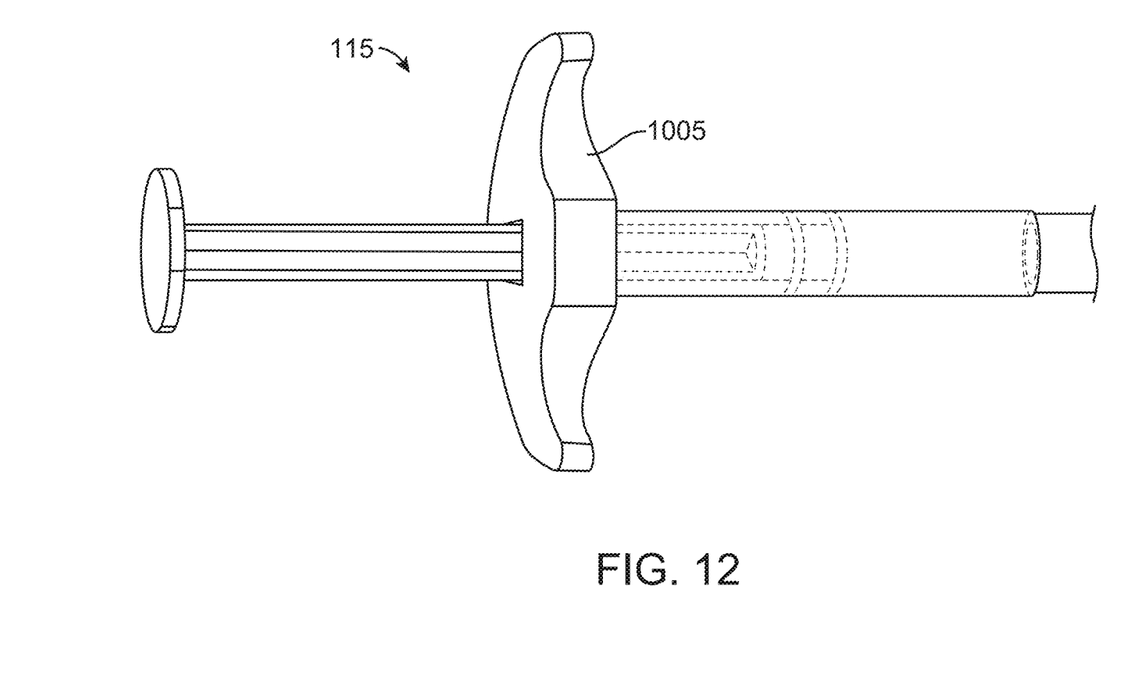

FIG. 2 shows the male syringe 115. At least a portion of the plunger rod assembly 135 is slidably positioned within the barrel 130. The plunger rod assembly 135 consists of (i) the plunger rod 212 and (ii) a distal plunger rod cap 202 and (iii) a proximal plunger 210. The plunger rod cap 202 can be used to actuate the plunger rod 212 within the barrel 130 such as by pushing or pulling on the plunger rod cap 202. The male syringe 115 also has a distal flange 216, which can be grasped by a user when operating the plunger rod assembly 135. The distal flange 216 can be optionally fitted with a flange extender 1005, which is shown in FIG. 10. As shown in FIG. 10, the flange extender 1005 is a flange structure that removably attaches to the distal flange 216 (FIG. 2) such as by sliding over the distal flange 216. FIGS. 11 and 12 shows the male syringe 115 with the flange extender 1005 coupled to the distal flange 216.

With reference again to FIG. 2, the contents of the male syringe 115 are positioned within the cavity of the barrel 130 at a location proximal of the plunger 210 of the plunger assembly 135. The plunger 210 pushes the contents of the barrel 130 out of an opening at a proximal end of the barrel 130. The proximal end of the barrel 130 forms a male coupler 205 that inserts into a corresponding female coupler of the female syringe 110 when the male syringe 115 and the female syringe 110 are coupled, as described more fully below. The male coupler 205 has a lumen that communicates with the cavity of the barrel 130 such that the contents of the barrel 130 can exit via the internal lumen of the male coupler 205.

The male coupler 205 is surrounded by a co-axial, annular sleeve 215 that is concentric with the male coupler 205 such that the sleeve 215 surrounds the male coupler 205. In the illustrated embodiment, the sleeve 215 is cylindrical although the shape may vary. A tip of the male coupler 205 extends proximally past the sleeve 215. An internal surface of the annular sleeve 215 is threaded such that it can couple with corresponding threads of the female syringe 110, as described below.

In an example embodiment, the male syringe is a TOP PAC syringe (or equivalent thereof) manufactured by Schott Schweiz AG.

FIG. 3A shows the female syringe 110, which is a prior art female syringe. The plunger rod assembly 125 consists of a plunger rod 312 and a distal plunger rod cap 302 and a proximal plunger 310. At least a portion of the plunger rod assembly 125 of the female syringe 110 can slide through the barrel 120 by actuating (such as pushing or pulling) the plunger rod cap 302 at a distal end of the plunger rod 312. As mentioned, the female syringe 110 has a proximal, female coupler 305 that is sized to receive therein the male coupler 205 (FIG. 2) of the male syringe 115. The barrel 120 of the female syringe 110 defines an internal cavity that secures the contents at a location proximal of the plunger 310 of the plunger rod assembly 125. When the female syringe 110 is in a standalone state as shown in FIG. 3A, the plunger 310 can be moved to a proximal-most position so that it abuts a proximal-most edge 315 of the internal cavity, as shown in FIG. 3A. When positioned as such, the plunger 310 of the plunger assembly 125 can push all the contents out of the barrel 120 via an opening in the female coupler 305.

Figure 3B:
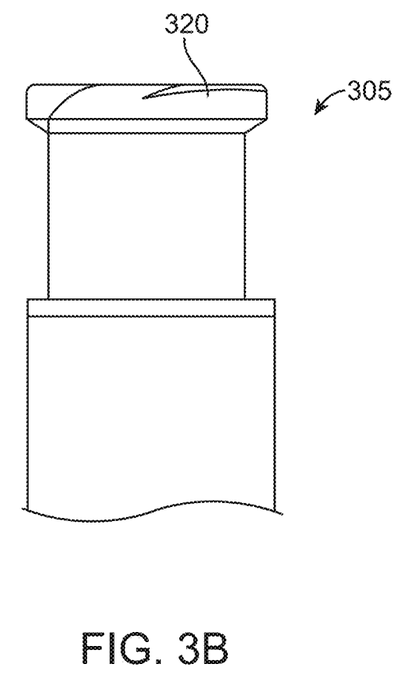
FIGS. 3B and 3C shows a female coupler portion of the female syringe of FIG. 3A.
Figure 3C:
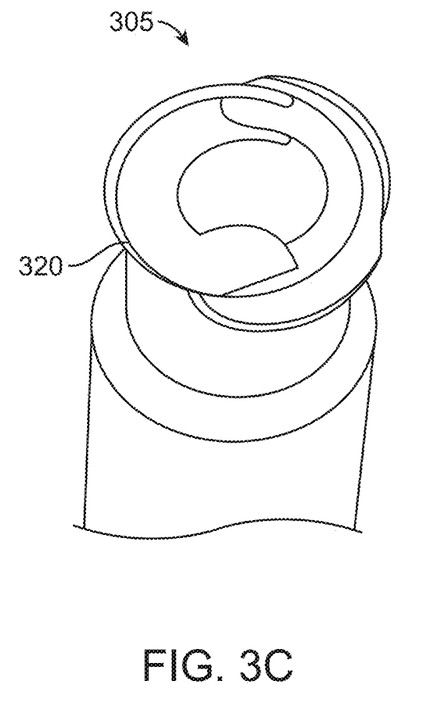

With reference still to FIG. 3A, the female coupler 305 is cylindrical with a lumen that can receive therein the male coupler 205 of the male syringe 115 (FIG. 2) in a male-female relationship. The female coupler 305 is threaded with a thread member 320 that threadedly couples with the corresponding threads of the internal surface of the annular sleeve 215 (FIG. 2). The female coupler 305 is sized and shaped to fit within the complementary-shaped sleeve 215 of the male coupler 205. In this manner, the female syringe 110 can securely couple to the male syringe 115 as shown in FIG. 1. The thread member 320 wraps around or encircles the entire circumference of the female coupler 305, as shown in FIGS. 3B and 3C, which show enlarged views of the female coupler 305.

Figure 4:
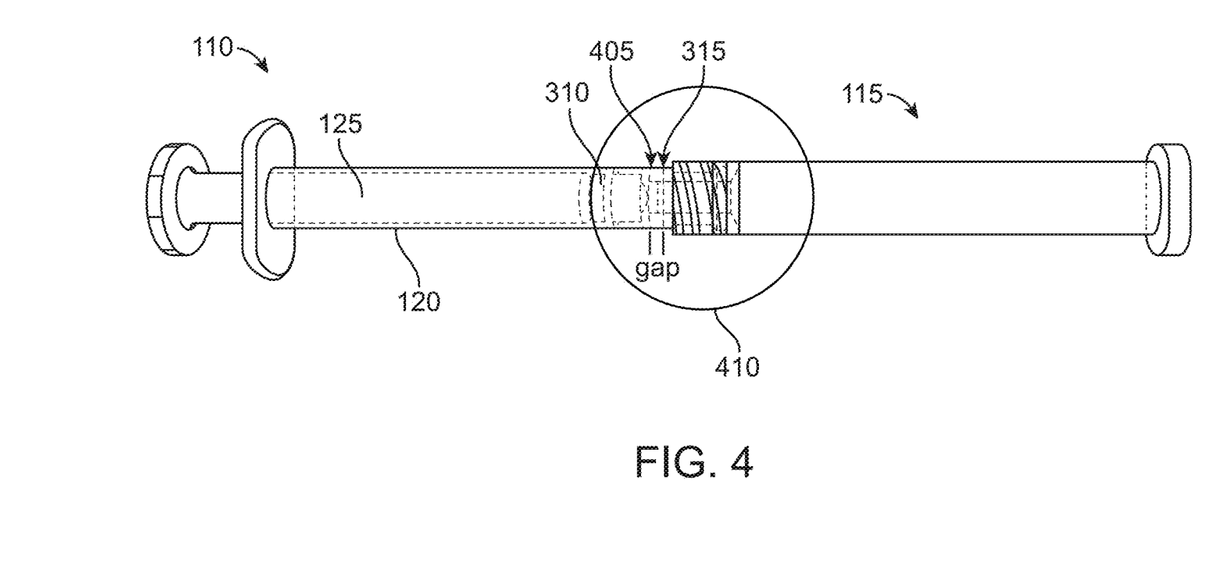
FIG. 4 shows the coupled male syringe and female syringe of the prior medication component mixing system of FIG. 1.

FIG. 4 shows the female syringe 110 and the male syringe 115 fully coupled to one another. The plunger rod assembly 135 of the male syringe is not shown in FIG. 4 although the plunger rod assembly 135 is present in the assembled device as shown in FIG. 2. When fully coupled as such, a proximal tip of the male coupler 205 (FIG. 2) extends or pokes into a proximal region of the barrel 120 of the female syringe 110. In this manner, the proximal tip of the male coupler 205 forms a stop against which the proximal-most edge 405 of the plunger 310 abuts when the plunger assembly 125 is depressed into the barrel 120 of the female syringe 110. In other words, the protrusion of the male coupler 205 into the barrel 120 prevents the plunger assembly 125 from being fully depressed into the barrel 120 in that it prevents the proximal-most edge 405 of the plunger 310 from contacting the proximal-most edge of the barrel 120.

Thus, as shown in FIG. 4, a gap 410 is formed between the proximal-most edge 405 of the plunger 310 and the proximal-most edge 315 of the internal cavity of the barrel 120 of the female syringe 110. The presence of the gap 410 can result in incomplete mixing of the dry contents of the female syringe 110 with the contents of the male syringe 115 as the plunger assembly 125 may be unable to fully transfer the contents between each syringe.

Improved Female Syringe

There is now described an example embodiment of an improved female syringe that overcomes the deficiencies of the prior art female syringe 110. The improved female syringe, referred to as female syringe 510 (FIG. 6), is structurally configured such that, when fully coupled with the male syringe 115, the male coupler 205 of the male syringe 115 does not and cannot extend into or otherwise penetrate the barrel of the female syringe 510, as described more fully below. Thus, the plunger assembly of the female syringe 510 can be fully depressed to the proximal-most end of the female syringe barrel to expel all of the contained contents even when the male syringe 115 is fully coupled to the female syringe 110.

Figure 5:
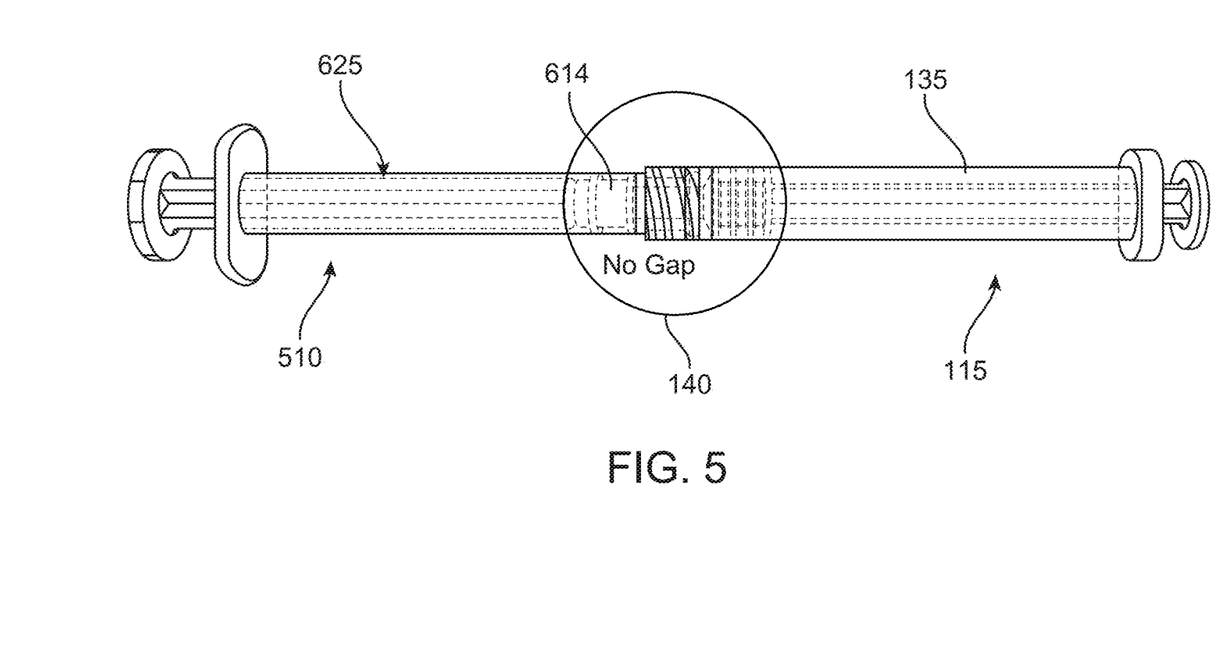
FIG. 5 shows an improved medication component mixing system.

FIG. 5 shows the female syringe 510 coupled to the male syringe 115 at a coupling region 140. As in the prior system, the female syringe 510 and the male syringe 115 can transfer their respective contents into one another when coupled as such for mixing. Note that, when fully coupled, a plunger assembly 625 of the female syringe 510 can be fully depressed such that a proximal-most edge of a plunger 614 can abut a proximal-most edge of a barrel 620 (FIG. 6) of the female syringe 510. Thus, as shown in circle 140 of FIG. 5, there is no gap between the proximal-most edge 405 of the plunger 310 and the proximal-most edge of the barrel of the female syringe 510 as in the prior art system. Moreover, when fully coupled, the male coupler of the male syringe 115 does not extend at all into the barrel of the female syringe 510.

Figure 6:
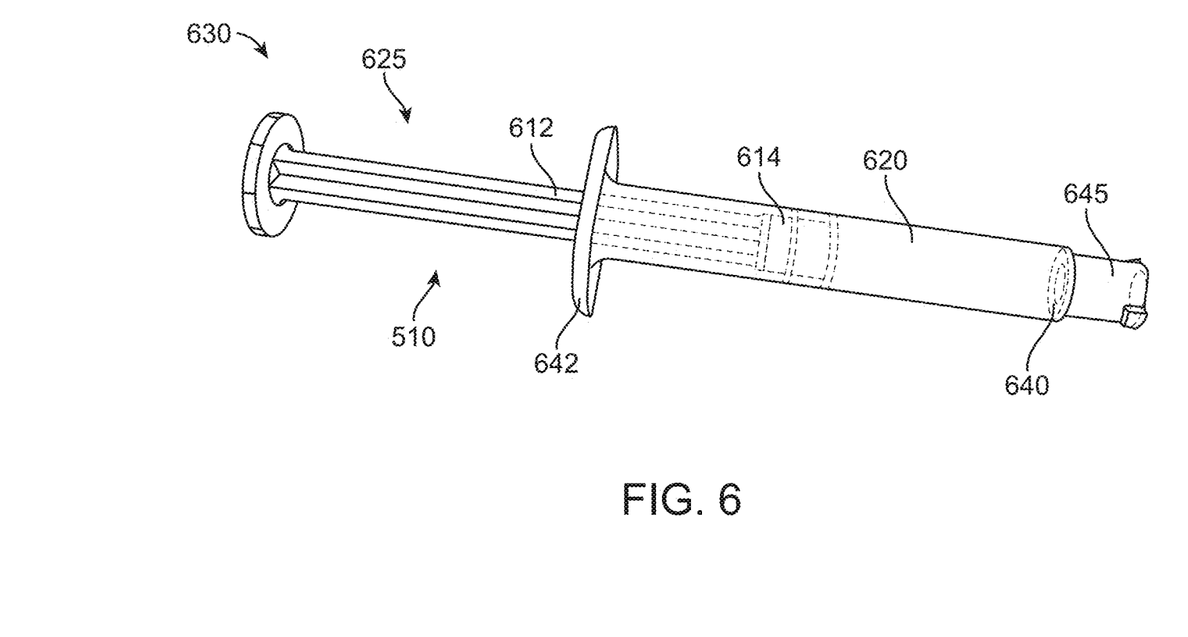
FIG. 6 shows an improved female syringe of the medication component mixing system shown in FIG. 5.

FIG. 6 shows the improved female syringe 510. As mentioned, the female syringe 510 includes the barrel 620 in which the plunger rod assembly 625 is slidably positioned. The plunger rod assembly 625 includes a plunger rod 612 having a distal rod cap 630 and a proximal plunger 614. The barrel 620 has an internal cavity defined by a proximal-most edge 640 of the barrel 620. The female syringe 510 has a distal flange 642, which can be optionally fitted with a flange extender, such as the flange extender 1005 shown in FIG. 10. As mentioned, the plunger rod assembly 625 can be fully depressed such that the proximal plunger 614 abuts the proximal-most edge 640 of the barrel even when the female syringe is fully coupled to the male syringe 115, as shown in FIG. 5.

Figure 7:
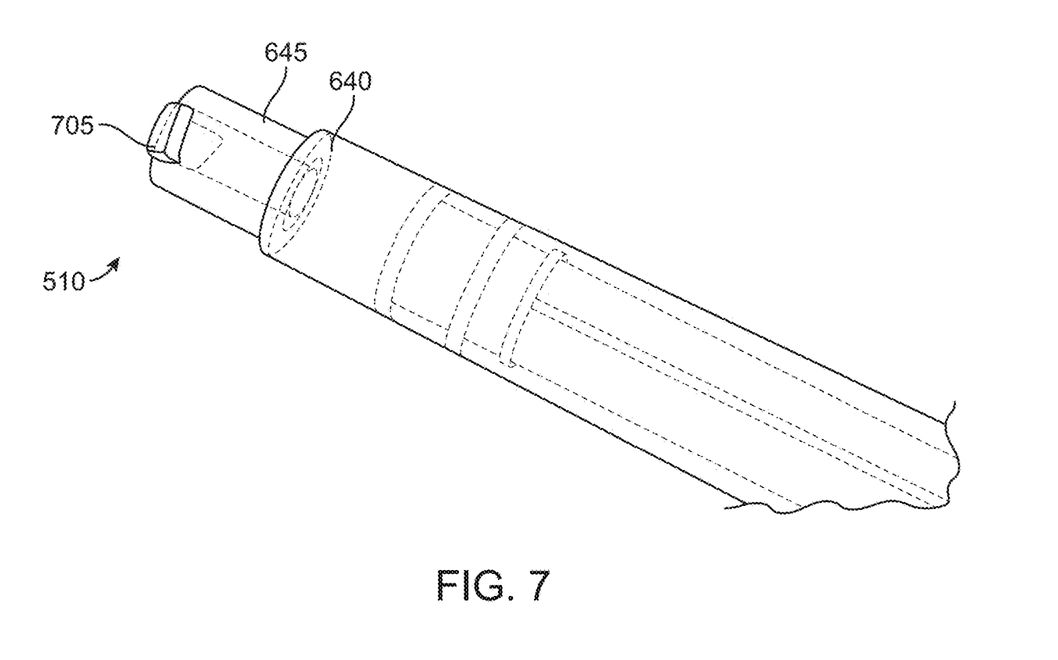
FIGS. 7 and 8 show enlarged views of a female coupler of the female syringe of FIG. 6.
Figure 8:
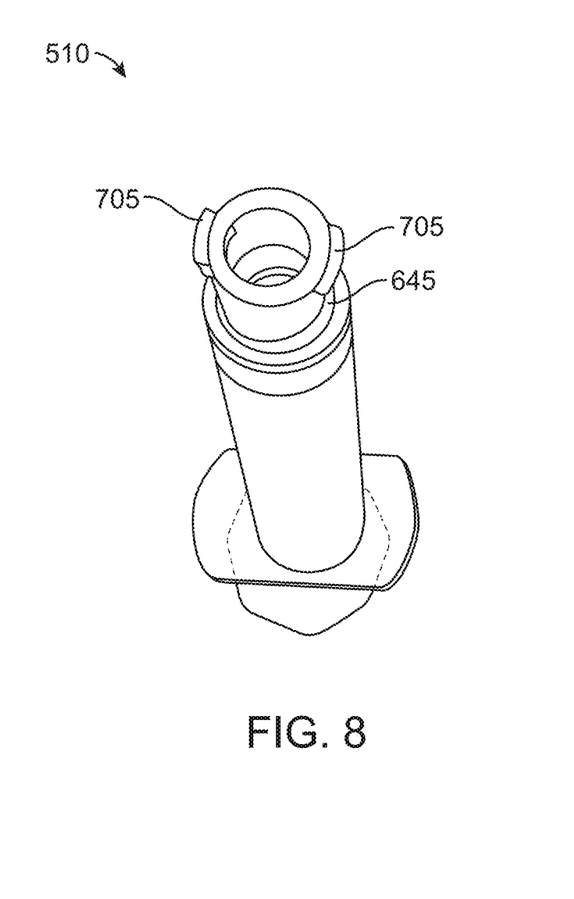

With reference still to FIG. 6, the female syringe 510 has a female coupler 645. FIGS. 7 and 8 show enlarged views of the female coupler 645 of the female syringe 510. The female coupler 645 contains an internal lumen that communicates with the cavity of the barrel 620. The female coupler 645 has at least one external thread member in the form of one or more lugs 705 positioned on opposed sides of the female coupler 645. The lugs 705 are sized and shaped to threadedly engage the corresponding threads on the internal surface of the annular sleeve 215. In an embodiment, the lugs are ISO compliant. The lugs 705 have a shape such that the lugs can be fully seated within the threads on the internal surface of the annular sleeve 215. That is, the lugs 705 can be threaded into the threads on the internal surface of the annular sleeve 215 only to a stop point at which point the male coupler will not and cannot extend into the barrel of the female syringe 510.

As best shown in the view of FIG. 8, the female coupler 645 of the female syringe 510 has a non-circular, tabular or at least partial cruciform shape when viewed along the longitudinal axis of the female syringe. In contrast, the female coupler 305 of the prior art female syringe 110 has a circular shape (as shown in FIG. 3C).

Figure 9:
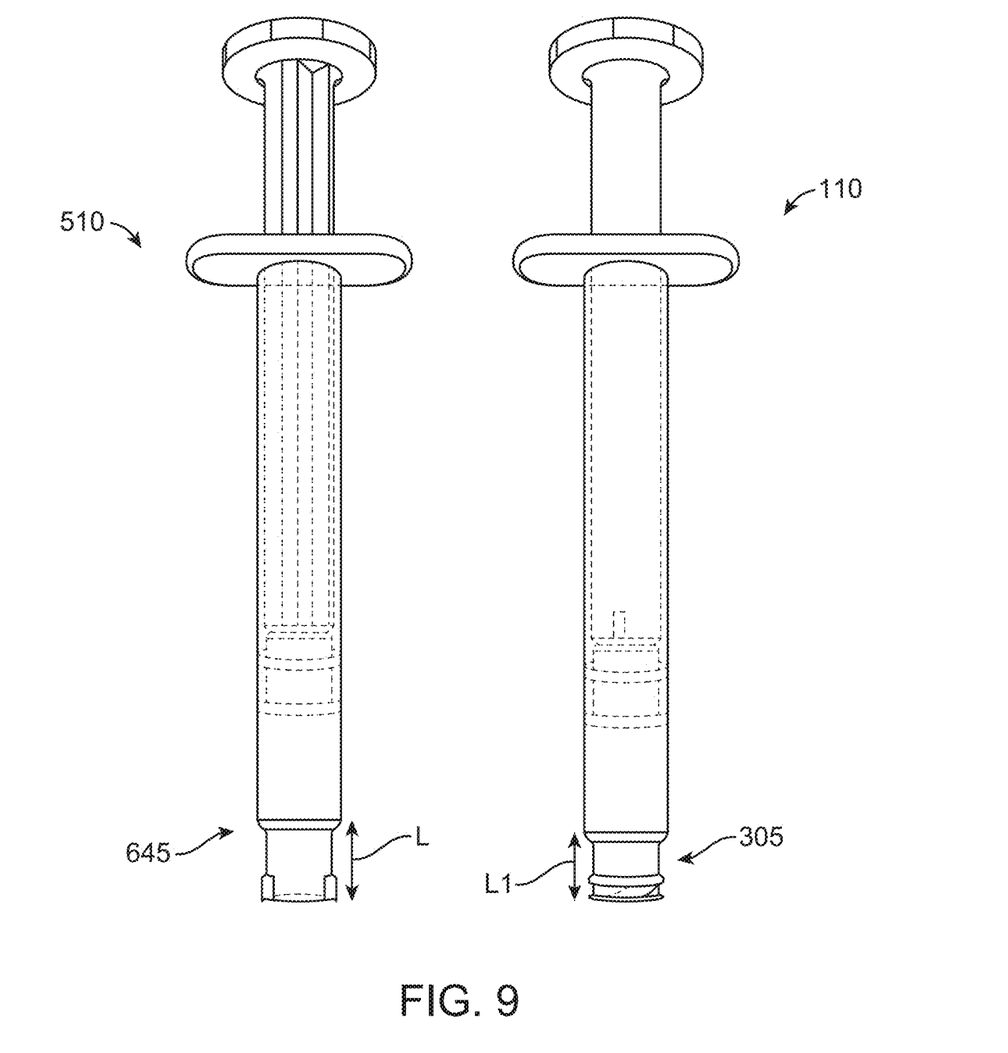
FIG. 9 shows the prior art female syringe and improved female syringe.

In addition, the female coupler 645 of the improved syringe 510 has a larger longitudinal length relative to a longitudinal length of the female coupler 305 of the prior art female syringe 110. FIG. 9 shows the prior art female syringe 110 and improved female syringe 510 in a side-by-side arrangement. As shown in FIG. 9, the female coupler 645 of the improved female syringe 510 has a length L that is longitudinally longer than the length L1 of female coupler 305 of the prior art female syringe 110. The female coupler 645 has a length that is selected to accommodate the length of a male coupler of a corresponding male syringe such that the male coupler of the male syringe does not and cannot extend into the barrel of the female syringe when the syringes are coupled to one another. In an example, the female coupler has a length that is longer (by an excess length) than the length of the annular sleeve 215 (FIG. 2) that surrounds the male coupler 205, wherein the excess length is equal to or greater than a protrusion length by which the male coupler 205 extends longitudinally beyond the annular sleeve 205.

In an embodiment, the female coupler 645 of the female syringe 510 contains a lumen that tapers from a narrow to wider diameter from the barrel toward the proximal tip of the female coupler 645. The male coupler of the male syringe has a complementary taper with a smaller diameter at the proximal tip relative to the distal base of the male member. This complementary taper physically limits insertion length of the male member into the female member and thereby prevents overtightening. Thus, the male coupler has an outer taper that matches or substantially matches a complementary taper of the inner lumen (i.e., the inner diameter) of the female member such that the complementary taper physically limits insertion length of the male member into the female member.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore, the spirit and scope of the appended claims should not be limited to the description of the embodiments contained herein.

The invention claimed is:

1. A female syringe system, comprising a female syringe formed of:
   (i) a barrel member defining an internal cavity and having an internal, proximal-most edge that defines a proximal-most edge of the internal cavity, the barrel member having a proximal opening through which contents can be expelled from the internal cavity;
   (ii) a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and
   (iii) a tapered female coupler on a proximal region of the barrel member, the tapered female coupler having an opening that receives a complementary tapered male member of a male syringe to couple the female syringe with the male syringe, wherein the female coupler has a structural configuration that prevents the complementary tapered male member of the male syringe from protruding into the internal cavity of the barrel member when the male syringe is coupled to the female syringe, wherein the structural configuration of the female coupler comprises at least one lug thread member that threadedly mates with a complementary thread of the male syringe, the at least one lug thread member positioned solely on a proximal-most edge of the female coupler; wherein the female coupler comprises a cylindrical body having an entirely smooth outer surface, the outer surface being entirely smooth except for the at least one lug thread; wherein the male syringe has a male syringe housing that defines both a male syringe internal cavity and a smooth annular sleeve of the male syringe that surrounds the complementary tapered male member of the male syringe; and wherein a longitudinal length of the female coupler is longer by an excess length than a length of the annular sleeve of the male syringe that surrounds the complementary tapered male member of the male syringe, wherein the excess length is equal to a protrusion length by which the complementary tapered male member extends longitudinally beyond the annular sleeve.

2. The system of claim 1, wherein the at least one lug thread member comprises two lugs on an outer surface of the female coupler.

3. The system of claim 1, wherein the female syringe comprises polypropylene.

4. The system of claim 1, further comprising the male syringe.

5. The system of claim 4, wherein the male syringe comprises a cyclic olefin copolymer and the female syringe comprises polypropylene.

6. The system of claim 1, wherein the tapered female coupler has a tapered internal lumen.

7. A female syringe system, comprising a female syringe formed of:
   (i) a barrel member defining an internal cavity and having an internal, proximal-most edge that defines a proximal-most edge of the internal cavity, the barrel member having a proximal opening through which contents can be expelled from the internal cavity;
   (ii) a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and
   (iii) a female coupler on a proximal region of the barrel member, wherein the female coupler couples to a male member of a male syringe, wherein the male syringe includes a smooth, concentric sleeve that surrounds the male member, and wherein the male member is longer in length than the concentric sleeve such that a tip of the male member extends past a tip of the concentric sleeve, and wherein the male member and the female coupler have complementary tapers that limit a depth of insertion of the male member into the female coupler, and wherein the female coupler includes at least one lug thread member that threadedly mates with a complementary thread of the male syringe, the at least one lug thread member positioned solely on a proximal-most edge of the female coupler wherein the female coupler comprises a cylindrical body having an entirely smooth outer surface, the outer surface being entirely smooth except for the at least one lug thread; wherein the male syringe has a male syringe housing that defines both a male syringe internal cavity and the concentric sleeve of the male syringe; and wherein a longitudinal length of the female coupler is longer by an excess length than a length of the annular sleeve of the male syringe that surrounds the complementary tapered male member of the male syringe, wherein the excess length is equal to a protrusion length by which the complementary tapered male member extends longitudinally beyond the annular sleeve.

8. The system of claim 7, wherein the female syringe comprises polypropylene.

9. The system of claim 7, wherein the male member does not extend into the barrel member of the female syringe.

10. The system of claim 7, further comprising the male syringe.

11. The system of claim 10, wherein the male syringe is made of cyclic olefin copolymers and the female syringe is made of polypropylene.

12. A female syringe system, comprising a female syringe formed of:
(i) a barrel member defining an internal cavity and having an internal, proximal-most edge that defines a proximal-most edge of the cavity, the barrel member having a proximal opening through which contents can be expelled from the internal cavity;
(ii) a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and
(iii) a tapered female coupler on a proximal region of the barrel member, the female coupler having an opening that receives a complementary tapered male member of a male syringe to couple the female syringe with the male syringe, wherein the female coupler has a structural configuration that prevents the male member of the male syringe from protruding into the internal cavity of the barrel member when the male syringe is coupled to the female syringe, wherein the female coupler comprises a cylindrical body having an entirely smooth outer surface except for at least one lug thread positioned solely on a proximal-most edge of the female coupler.

13. The system of claim 12, wherein the female syringe is at least partially made of polypropylene.

14. The system of claim 12, wherein the female coupler of the barrel member has a longitudinal length, and wherein the length is longer by an excess length than a length of an annular sleeve of the male syringe that surrounds the male coupler of the male syringe, wherein the excess length is equal to or greater than a protrusion length by which the male coupler extends longitudinally beyond the annular sleeve.

15. The system of claim 12, further comprising the male syringe.

16. The system of claim 15, wherein the male syringe is made of cyclic olefin copolymers and the female syringe is made of polypropylene.

17. The system of claim 12, wherein the female coupler has a tapered internal lumen.

18. A female syringe system, comprising a female syringe formed of:
(i) a barrel member defining an internal cavity and having an internal, proximal-most edge that defines a proximal-most edge of the cavity, the barrel member having a proximal opening through which contents can be expelled from the internal cavity;
(ii) a plunger slidably positioned at least partially within the internal cavity, the plunger having a proximal-most tip, wherein the plunger slides within the internal cavity such that the proximal-most tip slides toward the proximal-most edge of the barrel member in a manner that expels contents of the barrel member through the proximal opening of the barrel member; and
(iii) a female coupler on a proximal region of the barrel member, wherein the female coupler couples to a male member of a male syringe, wherein the male syringe includes a concentric sleeve that surrounds the male member, and wherein the male member is longer in length than the sleeve such that a tip of the male member extends past a tip of the sleeve, and wherein the male member and female coupler have complementary tapers that limit a depth of insertion of the male member into the female coupler, wherein the female coupler comprises a cylindrical body having an entirely smooth outer surface except for at least one lug thread positioned solely on a proximal-most edge of the female coupler.

19. The system of claim 18, wherein the female syringe is at least partially made of polypropylene.

20. The system of claim 18, wherein the male member does not extend into the barrel member of the female syringe.

21. The system of claim 18, wherein the female coupler of the barrel member has a longitudinal length, and wherein the length is longer by an excess length than a length of the sleeve of the male syringe, wherein the excess length is equal to or greater than a protrusion length by which the male coupler extends longitudinally beyond the sleeve.

22. The system of claim 18 further comprising the male syringe.

23. The system of claim 22, wherein the male syringe is made of cyclic olefin copolymers and the female syringe is made of polypropylene.

* * * * *